# (12) United States Patent
Nienow et al.

(10) Patent No.: US 6,395,516 B1
(45) Date of Patent: *May 28, 2002

(54) VESSEL FOR MIXING A CELL LYSATE

(75) Inventors: Alvin William Nienow, Birmingham; Antony Gordon Hitchock, Crewe; Grainne Lois Riley, Sussex, all of (GB)

(73) Assignee: Cobra Therapeutics Limited, Keele (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/522,631

(22) Filed: Mar. 10, 2000

Related U.S. Application Data (60) Provisional application No. 60/125,747, filed on Mar. 23, 1999.

(30) Foreign Application Priority Data

Mar. 11, 1999 (GB) .............................................. 9905646

(51) Int. Cl.⁷ ................................................ C12P 19/34
(52) U.S. Cl. ................... 435/91.1; 435/306.1; 366/318; 366/320; 366/322
(58) Field of Search ........................... 435/306.1, 91.1; 366/318, 320, 322

(56) References Cited

U.S. PATENT DOCUMENTS 5,248,485 A * 9/1993 Lilja et al. .................. 422/229

FOREIGN PATENT DOCUMENTS

| WO | 97/23601 | 7/1997 |
| WO | 97/29190 | 8/1997 |

OTHER PUBLICATIONS

EKATO Handbook of Mixing Technology—Impeller Systems, Published by Ruhr and Mischtechnik GmbH: ISBN code 920–02–269/1000.
Introduction to Mixing, Professor Barnes, 1989 0–59538032–0–1.
Birnboim, H.C., "A rapid alkaline extraction method for the isolation of plasmid DNA", *Methods Enzymol.*, 1983, vol. 100, pp. 243–255.
Birnboim, H.C. et al., "A rapid alkaline extraction procedure for screening recombinant plasmid DNA", *Nucleic Acids Res.*, 1979, vol. 7, No. 6, pp. 1513–1523.
Chase, E. et al., "Viscoelastic behavior of mammalian DNA", *Biophys. J.*, 1979, vol. 28, pp. 93–105.
Elson, T. et al., "X–ray studies of cavern sizes and mixing performance with fluids posessing a yield stress", *Chem Eng Sci.*, 1986, vol. 41, No. 10, pp. 2555–2562.
Hanahan, D., "Studies on transformation of *Escherichia coli* with plasmids", *J. Mol. Biol.*, 1983, vol. 166, pp. 557–580.
Kuboi, R. et al., "A multipurpose stirred tank facility for flow visualisation and dual impeller power measurement", *Chem. Eng. Commun.*, 1983, vol. 22, pp. 29–39.
Levy, M. et al., "Effect of shear on plasmid DNA in solution", *Bioprocess Engineering*, 1999, vol. 20, pp. 7–13.
Marquet, M. et al., "Process development for the manufacture of plasmid DNA vectors for use in gene therapy", *Bio Pharm*, Sep. 1995, pp. 26–37.
Tanguy, P. et al., "Finite element analysis of viscous mixing with a helical ribbon–screw impeller", *AIChE Journal*, 1992, vol. 38, No. 6, pp. 939–944.
Thomas, C. et al., "Action of shear on enzymes: Studies with alcohol dehydrogenase", *Biotechnology and Bioengineering*, 1979, vol. 21, pp. 2263–2278.
Uhlenhopp, E. et al., "Viscoelastic characterization of single–stranded DNA from *Escherichia coli*", *Biophysical Journal* 1975, vol. 15, pp. 223–232.
Van 't Riet, K. et al., "The trailing vortex system produced by rushton turbine agitators", *Chem. Eng. Sci.*, 1975, vol. 30, pp. 1093–1105.

* cited by examiner

*Primary Examiner*—James Ketter
(74) *Attorney, Agent, or Firm*—Woodcock Washburn LLP

(57) ABSTRACT

The invention relates to a vessel for mixing a cell lysate. The invention also relates to a method of using the vessel to mix a cell lysate in order to obtain high-purity products such as nucleic acids or proteins for use in a variety of applications. The invention also relates to a method for monitoring the degree of cell lysis in a cell suspension by measuring the viscosity of the cell suspension.

20 Claims, 4 Drawing Sheets

VESSEL FOR MIXING A CELL LYSATE

REFERENCE TO RELATED APPLICATIONS

This Application: claims benefit of U.S. provisional Application Serial No. 60/125,747, filed Mar. 23, 1999 and claims priority to United Kingdom 9905646.7, filed Mar. 11, 1999, all applications incorporated by reference herein in their entireties.

FIELD OF THE INVENTION

This invention relates to a vessel for mixing a cell lysate. The invention also relates to a method of using the vessel to mix a cell lysate in order to obtain high-purity products such as nucleic acids or proteins for use in a variety of applications.

BACKGROUND OF THE INVENTION

The alkaline lysis of bacterial cells is a well-established laboratory technique for recovering plasmid DNA from host cells (Birnboim et al., Methods Enzymol. 100, 243–255, 1983). The method involves the addition of a detergent, usually sodium dodecyl sulphate (SDS) and sodium hydroxide to a bacterial cell suspension followed by the addition of a strong neutralising solution, usually potassium acetate or glacial acetic acid, after a short period of incubation. This results in a solution containing large aggregates, also referred to as flocs, comprising denatured chromosomal DNA, protein, cell wall and/or membrane material. The flocs are removed from the solution by coarse filtration or centrifugation, leaving a solution containing plasmid DNA that can be further purified by a variety of standard procedures.

The method is based firstly on the chemical breakage of cell walls and membranes, followed by the solubilization and denaturation of cellular components in an alkaline solution. The ability of plasmid DNA to renature upon neutralisation and chromosomal DNA☐s inability to do likewise enables the isolation of plasmid DNA.

The method of alkaline lysis and the properties of the solutions produced at various stages of the alkaline lysis method have previously only been of academic interest. However, with the advent of human gene therapy, utilizing plasmid DNA obtained from host cells such as *E. coli,* there is now a requirement for the production of large quantities of very high purity plasmid DNA. The requirement of such large-scale manufacture has increased the need for new techniques so that the scale and robustness of operations can be increased to the level and standard required.

Chromosomal DNA is found in both prokaryotes and eukaryotes and is known to possess viscoelastic properties, which have previously been utilised to determine the size of the DNA molecules (Chase, et al., Biophys. J. 28, 93–105, 1979). The viscoelastic properties have also been recognised when the process of alkaline lysis has been used to isolate plasmid DNA from bacteria (Nienow, AIChE Annual Meeting, November 1998, Florida USA). One feature of the process is the change in the rheological properties of the solution at various stages of the procedure. Studies of these rheological properties have shown that the initial cell suspension exhibits Newtonian characteristics. The characteristics of a Newtonian fluid can be summarised by three criteria (1) constant viscosity, and when a fluid flows under laminar conditions: (2) shear stress is directly proportional to shear rate, and (3) the only stress generated is shear stress (Barnes et al., Introduction to Rheology, 1989 and Ciccolini et al., Biotechnology and Bioengineering, 60, 768–770, 1998). Cell suspensions have been found to have a viscosity that is very nearly constant, with a value very similar to that of water i.e. less than 3 mPa (Ciccolini et al., Biotechnology and Bioengineering, 60, 768–770, 1998). When the alkaline detergent solution is added, the properties of the solution change dramatically to give a solution that has a shear-dependent, relatively low apparent viscosity with a maximum value of about 22 mPas at a shear rate of 350 s$^{-1}$ when a solution of about 120 g wet cell weight l$^{-1}$ is lysed. Despite the solution's low apparent viscosity, it is highly viscoelastic and gives a large Weissenburg effect. The Weissenburg effect is also known as "rod climbing" and is defined as the effect created when a shaft or rod rotates in a viscoelastic solution (Barnes et al., Introduction to Rheology, 1989). A Newtonian fluid would be forced toward the outer sides of a vessel by inertia, whereas an elastic fluid climbs up the shaft as a direct consequence of the normal stress (a characteristic of a viscoelastic fluid) which acts like a hoop around the shaft. The viscoelastic properties of the lysate solution have been characterised using a rheometer operated under the oscillatory mode. The phase angle of the solution was found to be 58°, wherein 0° represents a solid and 90° represents an inelastic fluid. This demonstrates the elastic properties of the solution. The relatively low apparent viscosity in combination with viscoelasticity is very unusual as most viscoelastic fluids also exhibit high apparent viscosities. On neutralisation, the viscoelasticity of the solution breaks down so that it once again becomes of low viscosity, close to that of water, with no signs of viscoelasticity.

Whilst acting as a critical step in the recovery and purification of plasmid DNA, the lysis and neutralisation step have the potential for generating additional contaminants such as small fragments of chromosomal DNA and irreversibly denatured plasmid DNA.

The problems are, at least partially, pH and time-related, specifically with respect to the period for which the plasmid DNA can be incubated in the alkaline detergent solution. Extended exposure to the concentrated alkaline solution may result in the formation of denatured plasmid DNA (Birnboim & Doly, Nuc.Acids.Res., 7, 1513, 1979 and International Patent Application WO 97/29190). Denatured plasmid DNA cannot be readily purified from renatured plasmid DNA and its presence therefore leads to significant loss of functional plasmid yield. It is therefore important that mixing is sufficiently vigorous to ensure localised extremes of pH are avoided and that exposures to these conditions are minimised.

If mixing is too vigorous at any stage of the procedure, strands of chromosomal DNA are physically broken up. The chromosomal DNA may be fragmented to a size where the fragments may renature upon neutralisation and be carried forward into the recovery and purification procedure. The fragmented chromosomal DNA will contaminate the solution and create a significant purification problem as it has similar properties to plasmid DNA and cannot be readily separated by techniques such as chromatography to the level required by regulatory authorities responsible for clinical products. Also, if the mixing is vigorous during neutralisation, the flocs formed become too small, due to mechanical stress and cannot be readily removed by centrifugation or filtration.

Clearly, any mixing process must be able to achieve rapid mixing without creating unwanted chemical or mechanical damage to the plasmid DNA, in addition limiting the mechanical damage to the chromosomal DNA and ideally without creating mechanical damage of the flocculated material. Similar problems occur when isolating proteins form cell cultures.

During the process, significant volume changes occur. The alkaline detergent added to the cell suspension is usually equal to or double the volume of the initial suspension and the neutralisation solution is usually the same volume as that of the initial (cell suspension. Consequently, the initial cell suspension may only represent 25% of the final volume to be mixed.

Any mixing must take account of these changes in volume so that efficient mixing can be carried out over a wide range of volumes. In addition to this, and especially in systems where more than one impeller is in operation, steps are preferably taken in order to minimise air entrapment in the solution by impellers intersecting the air/liquid interface. Such entrapment may cause mechanical damage and fragmentation of the chromosomal DNA.

At the laboratory scale, the process of alkaline lysis is achieved by "gentle mixing" such as the inversion of a test tube or bottle. This technique is clearly limited in scale and subject to operator influence. However, some companies do carry out this operation using volumes of up to 5 l (Oral Presentation by Schleef M., Bio-Europe 1997, Cambridge, England, 1997).

If plasmid DNA or other desired cell derived products are to be generated in a pure form suitable for clinical trials, a scaleable method of carrying out mixing during the lysis procedure is required to overcome the problems detailed above.

Methods using static mixers have been described in, for example, International patent application WO 97/23601 but do not address the problems of plasmid quality, yield and purity.

General discussions of methods for mixing solutions in vessels during the lysis process have been made by Marquet et al., (Bio Pharm, September, 26–37, 1995), but do not provide any description or data of a system that addresses the problems detailed above.

SUMMARY OF THE INVENTION

The present invention provides a vessel and methods for generating plasmid DNA and other desired cell-derived products in scales suitable for, for example, clinical trials. The vessel and methods avoid chemical and mechanical damage to plasmid DNA (or the desired product) and mechanical damage to chromosomal DNA during mixing during the lysis procedure such that high-purity plasmid DNA or other desired products can be obtained.

In one aspect, the present invention relates to a vessel for mixing a cell suspension or cell lysate.

In another aspect, the present invention relates to a method for using the vessel disclosed above in the lysis of cells of a suspension wherein efficient mixing is obtained without generating mechanical stresses sufficient to lead to substantial fragmentation of chromosomal DNA or flocs of aggregated material.

In yet another aspect, the present invention relates to a method for monitoring the degree of lysis or neutralisation in a cell suspension comprising measuring the torque on the axle of the impeller.

In a further aspect, the present invention relates to a method for preparing plasmid DNA and other desired products by monitoring the degree of lysis or neutralisation.

In yet a further a aspect, the present invention relates to plasmids and proteins prepared using the vessels and methods disclosed herein.

In still a further aspect, the present invention relates to a sectioned helical ribboned impeller.

DETAILED DESCRIPTION

The present invention provides a vessel for mixing a cell suspension and/or a cell lysate containing chromosomal DNA and a desired product, wherein the vessel comprises:

(a) one or more low power number impellers positioned so that the impeller or impellers give even dissipation of energy throughout the contents of the vessel;

(b) one or more feedlines enabling the addition of fluids to a well-mixed zone formed around the distal end of one or more of the impellers; and (c) one or more baffles spaced substantially equally around the inner surface of the vessel, wherein the one or more baffles extend substantially parallel to the axis of rotation of the or each impellers.

Even dissipation of energy throughout the contents of the vessel achieves homogeneous mixing of the vessel contents.

The desired product can be a protein. It is well known to those skilled in the art that proteins can be isolated from cell cultures and suitable chemical extraction procedures are described in Falconer et al., (Biotechnology and Bioengineering, 53, 453–458, 1997); Falconer et al., (Biotechnology and Bioengineering, 57, 381–386, 1998); and Falconer et al., (Biotechnology and Bioengineering, 62, 455–460, 1998). Desired proteins include antibodies, cytokines hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens. Specific examples of these proteins include proinsulin, growth hormone, dystrophin, androgen receptors, insulin-like growth factor I, insulin-like growth factor II, insulin-like growth factor binding proteins, epidermal growth factor TGF-$\alpha$, TGF-$\beta$, PDGF, angiogenesis factors (acidic fibroblast growth factor, basic fibroblast growth factor and angiogenin), matrix proteins (Type IV collagen, Type VII collagen, laminin), phenylalanine hydroxylase, tyrosine hydroxylase, oncogenes (ras, fos, myc, erb, src, sis, jun), E6 or E7 transforming sequence, p53 protein, Rb gene product, cytokines (e.g. Il-1, IL-6, IL-8) or their receptors, viral capsid protein, and proteins from viral, bacterial and parasitic organisms which can be used to induce an immunologic response, and other proteins of useful significance in the body. The desired proteins are preferably proteins that can be readily renatured, for example, Rnase. Standard techniques for isolating and renaturing proteins can be used.

Preferably, however, the desired product is plasmid DNA.

The terms "mixing" and "agitate" as used herein refer to the mixing of the contents of the vessel of the present invention.

The term "vessel" as used herein means any receptacle capable of holding the cell suspension. The vessel may be of any shape suitable for mixing and is preferably cylindrical. Preferably, the vessel has a shallow rounded or dished bottom with a concave shaped internal wall. Alternatively, it is preferred that the vessel has a flat bottom. The vessel preferably is hermetically sealed and hermetically sealed vessels are well known to those skilled in the art.

The vessel of the present invention has at least one rotatable axle for rotating the impellers and may have more than one rotatable axle. The use of two or more axles in fermentation and other mixing vessels is well known and is applicable to the presently claimed vessel. Preferably, however, the vessel has one axle.

The term "a cell suspension" as used herein means a medium comprising cells. The term "lysate" as used herein refers to a medium wherein cells have been lysed.

The cells may be any cells capable of growth or maintenance in a medium and include prokaryotic and eukaryotic cells. Preferably, the cells are bacterial cells such as *E.coli*, mammalian cells such as HeLa cells, CHO cells and myeloma cell lines, and insect cells. Most preferably, the cells are prokaryotic cells or lower eukaryotic cells such as yeasts. The cells may be present on microcarrier beads. Suitable microcarrier beads for culturing cells are well known to those skilled in the art.

The term "chromosomal DNA" is used herein to indicate DNA that forms part of the chromosome of a cell or a fragment thereof.

The term "plasmid DNA" is used herein to indicate DNA that forms part of a plasmid contained in the cells and encompasses any form of plasmid DNA, including vectors such as episomal vectors (i.e. BPV), integrating vectors, and viral vectors such as adenovirus vectors and retroviral vectors, cosmids, YACs, BACs and PACs.

The term "impeller" as used herein, refers to an element, which on rotation in a liquid, causes mixing of the liquid. Preferably, the impeller has one or more blades for mixing the liquid. There are numerous different types of impellers with different types of blade. Suitable impellers for use in the present invention are described in the Ekato handbook of mixing technology—Impeller Systems, Ekato, (Published by Ruhr and Mischtechnik GmbH). Preferably, the impeller is an axial impeller. An axial impeller is defined as an impeller having an axial component in the flow it imparts. Such an axial component ensures that the impeller pumps the fluid in an axial direction drawing in the fluid axially and ejecting it so that the flow of the liquid moves along the sides of the vessel which are substantially parallel to the axis of rotation of the impellers. The impeller may be a helical ribbon type impeller as described in the Ekato handbook of mixing technology—Impeller Systems (supra). A helical ribbon impeller comprises a strip spiral or blade attached to the rotatable axle of the vessel with one or more bars. The helical ribbon impeller induces an axial flow by displacement and also creates a tangential flow.

The impellers used in the present invention are low power number impellers. The term "a low power number impeller" refers to an impeller having a low power number (Po), which is a property of the impeller/vessel configuration calculated according to the following formula.

$$Po = \frac{2\_NM}{\_N^3 D^5}$$

where

2_Nm is equal to the power (W)

Po is power number and is dimensionless

N is impeller speed (rps)

M is torque (Nm)

_is density of the liquid to be mixed (kg m$^{-3}$)

D is impeller length (m)

A low power number is herein defined as less than 2, more preferably less than 1 and most preferably less than 0.5 when measured in a Newtonian fluid, specifically water.

Figures 3, 3A, 4:
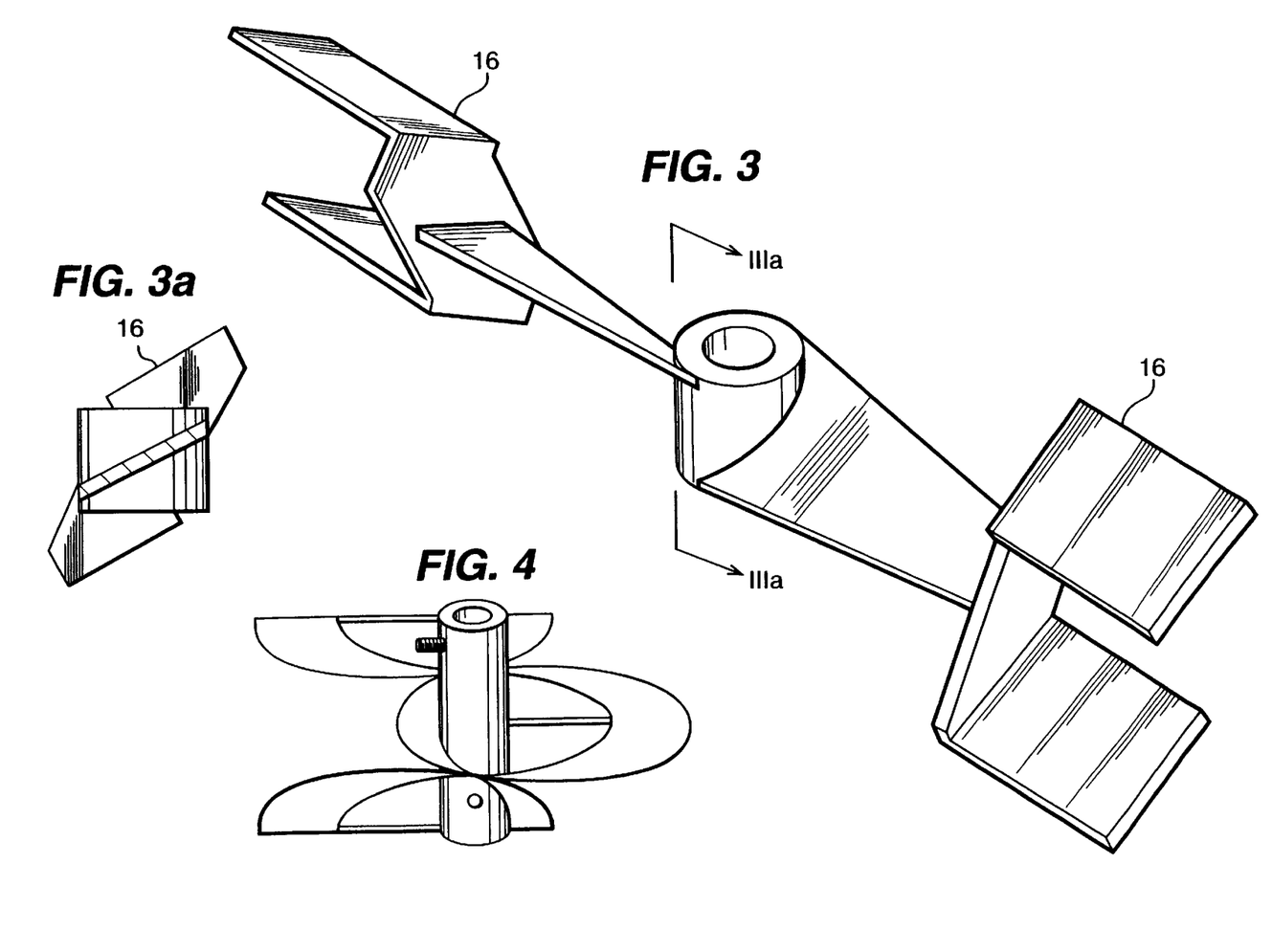
FIG. 3 shows the INTERMIG® impeller for use in the vessel of the present invention.
FIG. 3a shows the axle in cross-section.
FIG. 4 shows the sectioned helical ribbon impeller for use in the vessel of the present invention.

Preferably the impellers are the INTERMIG® impeller as manufactured by Ekato in Germany. An INTERMIG® impeller is an interference multistage counter flow impeller. The INTERMIG® has an outer double blade at each distal end and the double blade is arranged in a staggered position in a peripheral direction. The axial effect of the INTERMIG® impeller is increased by the staggering of the outer blades. An INTERMIG® impeller is shown in FIG. 3. Alternatively, the preferred impeller is a helical ribbon impeller as defined in the Ekato handbook of mixing technology—Impeller Systems (supra). The helical ribbon impeller may be a continuous helical impeller or may be modified so that subsequent to the addition of a liquid, none of the impeller intersects the air/liquid interface. This may be achieved by dividing the helical ribbon impeller into sections and separating the sections on the axle with gaps in between each section of the impeller thereby forming a sectioned helical impeller. Each section of the helical ribbon impeller can be seen as a separate impeller. The gaps between each section can correspond to the fluid level for certain volumes, such that the fluid meniscus for these volumes falls within a gap. A suitably modified sectioned helical ribbon impeller is shown in FIG. 4. The present invention also provides a sectioned helical ribbon impeller comprising two or more sections of a helical impeller which when present on an axle have a gap in between the sections which does not contain a blade or part of a blade of an impeller.

Preferably, the ratio of the impeller length to the internal diameter of the vessel is greater than 0.5, more preferably greater than 0.6.

The position of the one or more impellers in the vessel may also be important for achieving efficient mixing. The impellers are preferably positioned so that subsequent to any addition of a liquid to the vessel, none of the impellers intersect the air/liquid interface, thereby ensuring that turbulence of the air/liquid interface is reduced and the risk of introducing air bubbles into the cell suspension is also reduced.

Depending on the size of the vessel used, the number of impellers varies. For example, vessels having a volume of 1 to 5 l, preferably at least two impellers and more preferably at least 3 impellers are used. For vessels having a volume of 5 to 60 l, at least 3 to 5 impellers are preferably used. For vessels having a volume between 60 and 1000 l, at least 4 to 6 impellers are preferably used. However, if a continuous helical ribbon impeller is used, and as the helical ribbon impeller gives mixing throughout the vessel, it is possible to use only one continuous helical ribbon impeller for the vessel. However, the continuous helical impeller may optionally be used in combination with one or more non-helical ribbon axial impellers such as an INTERMIG® or propeller impeller, as defined in the Ekato handbook of mixing technology—Impeller Systems, Ekato (supra). Impellers are used in the vessel of the present invention in order to achieve mixing throughout the contents of the vessel and to avoid compartmentalisation at any point within the vessel. Compartmentalisation is the situation when there is a part of the vessel contents which is not being mixed with the rest of the vessel contents i.e. a compartment is formed in contents of the vessel which does not mix with the rest of the contents of the vessel. The round bottom or dished bottom of many vessels can be an area where compartmentalisation occurs. Preferably, an impeller is positioned adjacent to the bottom of such vessels to ensure that compartmentalisation does not occur. It is further preferred, especially when a continuous helical impeller is not used, that a separate impeller is used in each addition zone. The term "addition zone" refers to the section of the vessel filled when one of the three solutions, the cell suspension, lysis buffer and neutralisation buffer, is added to the vessel. The impeller set up of a vessel can be tested to determine if the impellers entrap air into the liquid and whether compartmentalisation occurs with the set power input limits. The vessel can be tested using standard visualisation techniques such as observation of the motion of tracer particles in transparent fluids, decolourisation and the use of X-ray photographic techniques in opaque fluids (Elson et al., Chem. Eng. Sci., 41, 2555–2562, 1986; Cronin et al., Food Bioprod. Proc. Trans. I. Chem. E., Part C, 72, 35–40; Smith et al., Chem. Eng, Sci., 39, 1093,1975; and Kuboi et al., Chem. Eng. Comm., 22, 29, 1983).

The term "well-mixed zone" refers to the area around each impeller in which liquid is caused to mix. The well-mixed zone can be determined by standard flow visualisation techniques, including observation of motion tracer particles in transparent fluids, decolourisation and the use of X-ray photographic techniques in opaque fluids (Elson et al., Chem. Eng. Sci., 41, 2555–2562, 1986; Cronin et al., Food Bioprod. Proc. Trans. I. Chem. E., Part C, 72, 35–40; Smith et al., Chem. Eng, Sci., 39, 1093,1975; and Kuboi et al., Chem. Eng. Comm., 22, 29, 1983). The well-mixed zone is preferably the area around each impeller where the greatest flow occurs. The well-mixed zone is preferably adjacent to the distal end of the impeller or impellers.

The term "feedline" as used herein, refers to an element capable of delivering fluids to a well-mixed zone. The vessel may comprises one or more feedlines enabling the addition of fluids to a well-mixed zone. A well-mixed zone is generally found adjacent to the distal end of one or more of the impellers. The feedlines may be a tube or a series of tubes that are present on the inner wall of the vessel and allow the delivery of fluid at substantially the same level in the vessel as an impeller. The fluid is delivered via the tube or tubes to substantially the same level within the vessel as the level of the impeller and is therefore considered to be delivered adjacent to the distal end of one or more of the impellers and into a well-mixed zone. Preferably, the fluid is delivered via the tube or tubes adjacent to the distal ends of two or more impellers. It is further preferred that there is at least one feedline for each impeller and/or at least one feedline for each addition zone. In the smaller vessels, i.e. less than 10 l, one point of addition at the level of the one or more impellers will be sufficient. However, in larger vessels, i.e. greater than 10 l it is preferred that fluids be introduced into the vessel at the level of the impeller at numerous points around the inner wall of the vessel. One way of achieving this is by introducing the fluid via annular sparge lines so that fluid enters simultaneously via a large number of ports positioned adjacent to the arc formed by the distal end of the impeller on rotation of the impeller. Another way is by using multiple ports at the level of each impeller. The tube or tubes forming the feedlines may be moveable within the vessel so that the level at which fluids are added can be altered during mixing.

It is further preferred that the feedline is so formed as to direct fluid being added towards the impeller.

In an alternative embodiment, the feedline is a conduit within the axle carrying the impellers which passes through one or more impellers to deliver the liquid adjacent to the distal end of the one or more impeller.

Preferably, the feedlines all deliver fluid to the zone of greatest mixing generally formed around the distal end of one or more impellers.

Preferably, the feedlines allow addition of each of the solutions to the vessel in less than 2 minutes.

The term "aspect ratio" as used herein, refers to the ratio of the height of the liquid within the vessel to the width of the liquid in the vessel. Where the vessel does not have a uniform height or width, the maximum width and height may be used to calculate the aspect ratio. In a specific embodiment of the invention, the vessel has an aspect ratio in the range of 0.5 to 2.5. By having a low aspect ratio, the vessel further enhances efficient mixing. In a particularly preferred embodiment, the aspect ratio of the vessel is 1.0.

The term "baffle" as used herein, refers to an element, which diverts the flow of liquid in the vessel. Baffles help to prevent the rotation of liquid inside the vessel, encourage top to bottom secondary flows and prevent the formation of a central vortex and subsequent air entrapment. The development of top to bottom secondary flows are important for mixing throughout the vessel as additional quantities of fluid are added sequentially and each must be homogenised throughout the whole contents of the vessel efficiently. The most common type of baffle is a strip of material having a width of approximately 10% of the internal vessel diameter, which extends along the length of the vessel in a direction substantially parallel to the axis of rotation of the one or more impellers. The edge of the baffles may be flush against the internal wall of the vessel or may be spaced away from the wall by a gap of approximately 0.1 to 5 cm. However, other types of baffles can also be employed such as those described by Nagata (Mixing Principles and Applications. John Wiley, New York, USA, 1975). The vessel has one or more baffles spaced substantially equally around the inner surface of the vessel, wherein the one or more baffles extend substantially parallel to the axis of rotation of the impellers. Preferably at least two baffles and more preferably at least four baffles are used in the vessel. Preferably, the baffles extend along the entire length of the vessel. The baffles are preferably 3 to 15%, more preferably 6 to 12% and most preferably 10% of the internal diameter of the vessel in width. The edge of each baffle may be flush with the inner wall of the vessel or may be spaced away from the inner wall of the vessel. The position of the baffles is preferably so that there is a close clearance between the baffles and the arc formed by the distal end of an impeller on its rotation. Preferably, the close clearance is between 0.1 and 10 cm, more preferably between 1 to 5 cm. In a particularly preferred embodiment, when the vessel has an internal diameter of about 0.45 meters and a volume of 60 l, it is preferred that there are 4 baffles, each having a width of 10% of the internal vessel diameter.

The use of baffles in mixing vessels is described in Ekato handbook of mixing technology—Impeller Systems, Ekato (supra) and in Nagata (Mixing Principles and Applications, Wiley, New York, 1975).

The term "substantial fragmentation" as used herein, refers to the fragmentation of chromosomal DNA to a level where the level of fragmented DNA in the purified product exceeds 4% of the weight of the desired product. In particular, when the desired product is plasmid DNA the term "substantial fragmentation" as used herein, refers to the fragmentation of chromosomal DNA to a level where the level of fragmented DNA in the purified product exceeds 4% of the total DNA content by weight when the plasmid DNA is purified according to the method of International Patent Application WO 97/29190. When the desired product is a protein the level of chromosomal DNA contamination is measured after the protein has been purified according to the method of Falconer et al., (Biotechnology and Bioengineering, 53, 453–458, 1997). Preferably, when the desired product is a protein, the level of chromosomal DNA contamination is less than 0.5% of the purified protein by weight.

The vessel preferably has a volume between 5 l and 1,000 l, more preferably between 50 l and 500 l and most preferably between 50 l and 100 l. Suitable lysis vessels are manufactured by Yateson Engineering Ltd. Bolton, United Kingdom.

The present invention also provides a method for using of the vessel of the present invention in the lysis of cells of a cell suspension, which contains chromosomal DNA and a desired product, wherein the one or more impellers are rotated at a speed selected such that efficient mixing is obtained without generating mechanical stresses sufficient to lead to substantial fragmentation of chromosomal DNA or flocs of aggregated material. Preferably, the desired product is plasmid DNA.

The method of the present invention preferably comprises adding the cell suspension to the vessel, mixing the cell suspension, adding a lysis solution to the cell suspension, mixing the cell suspension until the cells have lysed, adding a neutralising solution and mixing until neutralisation is achieved and flocs of aggregated material are generated. On neutralisation, the plasmid DNA is renatured. The plasmid DNA can then be further purified using standard processes such as bag filtration and chromatography, which are well known to those skilled in the art.

In the method of the present invention, it is preferred that the solutions added to the vessel are added using feedlines that are immersed within liquid contained in the vessel. Preferably, each solution is mixed in the vessel in less than 4 minutes, preferably in less than 2 minutes.

The cell suspension can be any cell suspension in any medium. Preferably the cell suspension has a cell density of 70 to 300 g wet weight $l^{-1}$.

The cell suspension is preferably mixed to generate and maintain a homogeneous solution. Preferably, the cell suspension is mixed whilst the lysis solution is added. The lysis solution is preferably a mixture of sodium hydroxide and SDS. Preferably, the lysis solution is added according to the method described in International Patent Application WO 97/29290. The combination of the high pH and the detergent results in lysis of cells and denaturation of chromosomal DNA as well as other cellular components. Preferably, the lysis solution is mixed with the cell suspension to generate a lysate in as short a period as possible to minimise the exposure to high pH levels present in the lysis buffer and thereby reduce the formation of irreversibly denatured plasmid DNA but not sufficiently high to cause mechanical damage to the chromosomal DNA.

Once lysis is complete, the viscoelastic properties of the resultant lysate will have dramatically increased and this can be used as a measure of the completion of lysis. The increase in viscoelastic properties may be visualised directly by observing the Weissenburg effect of the fluid climbing up the shaft of the impeller. This may also be measured indirectly, but more objectively, by monitoring the torque on the stirrer motor of the lysis vessel. By torque is meant the turning moment exerted by the motor of the impeller axle.

Whilst mixing the unlysed cell suspension, which behaves as a low viscosity Newtonian fluid, a stable low level of torque is observed. Upon lysis, the torque rises rapidly until lysis is complete, when it stabilises at a maximum value.

Accordingly, this aspect of the invention provides a method for monitoring the degree of lysis of a cell suspension in a vessel whose contents are mixed by rotating one or more impellers, comprising measuring the torque applied to the axle of the impeller, wherein the torque increases in proportion to the degree of cell lysis until lysis is complete, when it stabilises at a maximum value. Once lysis is complete, the viscoelastic properties of the resultant lysate will have dramatically increased and this can be used as a measure of the completion of lysis. On lysis, the torque generally increases between five and fifteen-fold (i.e. 500–1500%) before stabilising at a constant value. Preferably, a rise of greater than 300% of the initial torque is indicative of lysis, more preferably greater than 500%, even more preferably greater than 1000% increase.

When lysis is complete, or after a short, pre-determined period of incubation, preferably 1 to 60 minutes, more preferably 2 to 20 minutes and most preferably 5 to 10 minutes, the addition of a neutralisation buffer through the appropriate delivery feedline is initiated. The neutralisation buffer can be any strong organic acidic buffer such as glacial acetic acid. Preferably, the neutralisation buffer is 3M KAc, 10 mM EDTA pH 5.5. Preferably, the neutralisation buffer is added while the lysate is being mixed. Efficient mixing and neutralisation can be visualised directly, this time by disappearance of the Weissenburg effect due to a loss in viscoelastic properties of the lysate.

Again, this effect may be measured by monitoring the change in torque on the stirrer, which is seen to fall rapidly on neutralisation as the rheological properties of the lysate return to those of a low-viscosity Newtonian fluid. In the method of this aspect of the invention, complete neutralisation of the cell lysate is generally indicated by a decrease in torque, preferably to less than 50% of the maximum torque on the axle during the lysis stage of the reaction. More preferably, a drop to less than 30% of the maximum value achieved, most preferably to less than 25% of the maximum value, is indicative of neutralisation.

Complete neutralisation is important, since failure to return the fluid to one with a viscosity of less than 3 mPas and negligible viscoelastic properties results in poor filtration characteristics in subsequent purification steps and a decrease in overall yield.

Accordingly, a further aspect of the present invention provides a method for preparing a desired product from a cell suspension in a vessel, comprising the steps of lysing said cells by alkaline lysis to give a cell lysate, neutralising said cell lysate and preparing the desired product from the cell lysate, wherein the contents of said vessel are mixed by rotating one or more impellers, and wherein progress of the lysis and neutralisation reactions is monitored by measuring the torque applied to the axle of the impeller.

As the skilled reader will appreciate, torque may be measured using any measure of energy input as related either directly or indirectly to mechanical resistance in the contents of the vessel. For example, the increase in viscoelastic properties may be visualised directly by observing the Weissenburg effect of the fluid climbing up the shaft of the impeller. This may also be measured indirectly, but more objectively, by monitoring the torque on the stirrer motor of the lysis vessel. In the case of an electric motor-driven impeller, torque may conveniently be monitored by measuring the increased current drawn to maintain a constant speed of impeller rotation. In a preferred embodiment of this aspect of the invention, a rheometer is used to measure torque and thus monitor the progress of the reaction.

The plasmid contained in the cells may be any plasmid or vector as indicated above but is preferably a nucleic acid vector comprising DNA. The plasmid may be of linear or circular configuration and may be adapted for episomal or integrated existence in the host cell as set forth in the extensive body of literature known to those skilled in the art.

The present invention also relates to a plasmid obtained from a cell culture lysed using the vessel of the present invention.

The present invention also relates to a protein from a cell culture lysed using the vessel of the present invention.

The present invention is now illustrated in the following examples with reference to the Figures:

Materials and Methods

Construction of Therapeutic Expression Plasmid Vector pTX0161 pTX0161 is a high copy number (ColE1 origin of replication) plasmid vector carrying the *Escherichia coli* B nitroreductase gene (ntr) driven by the cytomegalovirus immediate early promoter. Delivery of this vector to mammalian tumour cells allows specific cell killing by the prodrug CB 1954 (Drabek et al., Gene Therapy, 4, 93–100, 1997), a form of enhanced cancer chemotherapy described as gene directed enzyme-prodrug therapy or GDEPT. pTX0161 was constructed by the removal of the ntr cassette from pTX0160 (Williams et al., Nuc, Acids Res., 26, 2120–2124, 1998) as an ApaI-blunted, XbaI restriction enzyme digested fragment which was then inserted into pTX0003 (a pUC19 derived vector encoding tetracycline resistance).

Generation of the Production Strain; DH1 pTX0161

10 ng of pTX0161 plasmid DNA was used to transform calcium competent *E. coli* DH1 cells (Hanahan, Mol. Biol., 166, 557–580, 1983). A single transformant was selected to generate a Master Cell Bank (MCB) of the Production Strain under conditions of Good Manufacturing Practice. Cells harvested from an exponentially growing culture, were cryopreserved in 20% glycerol and stored at −80° C. to constitute the MCB.

Fermentation of DH1 pTX0161

Inoculum Preparation

A 1 ml vial of DH1 pTX0161 was taken from the MCB and thawed rapidly at 37° C. The contents of this vial was aseptically inoculated into 5 ml of LB medium (Peptone 10 g/l, Yeast Extract 5 g/l, NaCl 5 g/l) supplemented with tetracycline (12 $\mu gml^{-1}$) in a 30 ml universal bottle. This was incubated at 37° C. in an orbital shaker (200 rpm). During mid-exponential growth phase, 4 ml of this culture was used to inoculate 46 ml of Terrific broth (Tartof and Hobbs, Focus, 9, 2–12, 1987) supplemented with tetracycline (12 $\mu gml^{-1}$) in a 500 ml Erlenmeyer flask. This was grown, as above, before being subcultured in two stages (200 ml and 2000 ml cultures in Terrific broth with tetracycline) and used to inoculate the fermenter once grown to a cell density of 2 $OD_{600\ nm}$.

Fermentation

A rich complex batch medium consisting of final concentrations of $KH_2PO_4$ (3 g/l), $Na_2HPO_4$ (6 g/l), NaCl (0.5 g/l), Peptone (2 g/l), $(NH_4)_2SO_4$ (10 g/l), polypropylene glycol, molecular weight 2025 g (0.2%), Trace element solution (0.05% [consisting of $CoCl_2.6H_2O$ (2 g/l), $CuCl_2.2H_2O$ (1.9 g/l), $H_3BO_3$ (1.6 g/l), $MnSO_4.H_2O$ (1.6 g/l), $Na_2MoO_4.2H_2O$ (2 g/l), $ZnCl_2.7H_2O$ (2 g/l), $Fe_2(SO_4)_3.x$ $H_2O$ (1 g/l), $CaCl_2.2H_2O$ (1 g/l), and Citric acid (60 g/l)]), $CaCl_2.2H_2O$ (0.03 g/l), $FeSO_4.7H_2O$ (0.04 g/l), citric acid (0.02 g/l) and yeast extract (20 g/l) was prepared and made up to a volume of 46 l in the fermentation vessel. After sterilisation in situ, aseptic additions of glycerol 2.8%), $MgSO_4$ (0.5 g/l) and vitamin solution (5 ml/l [consisting of biotin 0.6 g/l, folic acid 0.04 g/l, pyridoxine-HCl 1.4 g/l, riboflavin 0.42 g/l, pantothenoic acid 5.4 g/l, niacin 6.1 g/l]) and tetracycline (12 mg/l) were made. The vessel was then inoculated as above. Fermentation was carried out at 37° C., pH 6.8 with the dissolved oxygen setpoint 50% of air saturation. The vessel was sampled regularly and the $OD_{600nm}$ recorded to allow calculation of the specific growth rate. Plasmid DNA was isolated from samples during culture for qualitative analysis and from fermentation end-points for quantitative comparision (Qiagen Maxi plasmid purification kits, Qiagen Ltd.). Dry weight determination was used to estimate biomass.

Plasmid Copy Number Estimation

The molecular weight of pTX0161, a 7796 base plasmid, is $5.06 \times 10^6$ Daltons. The specific recovered plasmid yield can be converted to a recovered plasmid copy number, knowing that 1 $OD_{600nm}$ unit is equivalent to $2 \times 10^8$ cells $ml^{-1}$ for this fermentation culture (Kech and Brent, Current Protocols in Molecular Biology, Ausubel et al., Eds, John Wiley Sons Inc., New York, 1.2.2, 1995).

Fermentation Cell Harvesting

Cells were harvested when in late exponential growth phase by centrifugation at 5000 g for 25 minutes at 4° C. in sterile 1000 ml centrifuge bottles. The clarified supernatant was discarded and the cell pellets were either frozen at −80° C. or removed from the pots and transfer into bags prior to freezing.

Manual Lysis Procedure

The manual lysis procedure used as a comparison with the lysis vessel procedure is the Qiagen Midi and Maxi protocol (Qiagen Plasmid Purification Handbook 1997).

Primary Plasmid DNA Recovery by Modified Alkaline Cell Lysis

Preparation of a Cell Suspension for 5 l Cell Lysis

A total of 180 g (wet weight) of cells were removed from storage at −80° C. and thawed at 18° C. for approximately 20 minutes. Cell suspension buffer (50 mM Tris 10 mM EDTA at pH 8.0) was added to each centrifuge bottle sufficient to solubilise the cell pellet. Resuspended cells were pooled and mixed with a Silverson high shear mixer to generate a homogeneous suspension. The volume was then adjusted (by weight) with cell suspension buffer to 1 liter, a final cell concentration of approximately 180 g cell wet weight $1^{-1}$ cell suspension buffer.

Preparation of a Cell Suspension for 60 l Cell Lysis

A total of 1800 g (wet weight) of cells were removed from storage at −80° C. and thawed at 18° C. for approximately 20 minutes. The cell paste was removed from the bags and added to 9 l of cell suspension buffer (50 mM Tris 10 mM EDTA at pH 8.0). The cells were then suspended into the buffer using a Silverson High shear mixer to generate a homogeneous suspension. The volume of the cell suspension was then adjusted (by weight) with cell suspension buffer to 15 liters, a final cell concentration of approximately 120 g cell wet weight $1^{-1}$ cell suspension buffer.

Bag Filtration

The contents of the holding vessels was pumped through a 100 $\mu m$ woven nylon bag filter (Plastok Holdings Ltd) prior to 5_m filtration via a Polyguard depth filter (Millipore UK Ltd. Watford, England).

Expanded Bed Adsorption Chromatography

A Streamline 50 chromatography column (Pharmacia) was packed with 480 ml of DEAE Streamline (Pharmacia).

The chromatography bed was expanded using 0.1M NaOH by upward linear flow at a rate of 105 cmhr$^{-1}$, stopped to allow overnight sanitisation and re-expanded in equilibration buffer (0.8 M KAc, 10 mM EDTA pH 5.5) to prepare the column for loading. The plasmid containing filtrate was pumped onto the column at the same linear flow rate. Once loaded, the column was washed with equilibration buffer until the on-line absorbance detector (optical density at 254 nm or OD$_{254\ nm}$) was reduced to 20% of the maximum value or less. The column was then washed with a low salt buffer (25 mM Potassium acetate, 10 mM EDTA pH5.5) and the fluid flow direction was reversed. This allows packing of the chromatography gel in the column and reduces the buffer volumes required for subsequent steps. Washing was continued until 5% of the maximum OD$_{254\ nm}$ value was reached before residual RNA fragments were eluted from the column using 0.5M salt wash buffer (25 mM Potassium acetate, 10 mM EDTA, 0.5M NaCl pH 5.5). Plasmid DNA was then eluted with elution buffer (0.75 M NaCl, 25 mM KAc 10 mM EDTA pH 5.5) and stored overnight at +4 to +8° C.

Concentration of the Streamline Eluate

An Pellicon XL ultrafiltration device (Millipore UK Ltd, Watford, England) was sanitised with 0.1M NaOH and flushed with elution buffer. The plasmid enriched Streamline column eluate was concentrated approximately 25 fold by ultrafiltration using a 30 Kilodalton molecular weight cut off membrane. The concentrate was decanted and the system flushed with buffer to remove residual plasmid DNA which was pooled with the concentrate. The pool volume of ~50 ml was stored at 4–10° C. overnight.

Size Exclusion Chromatography

To remove residual contaminants such as digested RNA fragments, and in order to exchange the plasmid into a suitable formulation buffer, the concentrated Streamline eluate was loaded onto an Pharmacia XK16 column packed with approximately 112 ml of Pharmacia S500HR media (bed height 56 cm). The column pipework had been previously sanitised with 0.1M NaOH, and equilibrated with 0.3M NaCl. The entire concentrate was loaded onto the column at 1.2 ml/minute. The OD$_{254\ nm}$, of the column eluate was monitored throughout the run and 2 ml fractions collected. Material in the first OD$_{260\ nm}$ peak were regarded as being pure plasmid DNA and were pooled. The volume of the pool was approximately 20–25 ml. Samples for quality control analysis were removed and the remainder of the bulk plasmid pool aliquoted and frozen at −80° C.

DNA Analysis for Quality Control
Product Concentration

The total nucleic acid concentration (strength of solution) was determined spectrophotometrically by recording the optical density at 260 nm and converting this value to mg/ml assuming that the extinction coefficient of a 0.0005% solution of plasmid DNA in a 1 cm path length cell is 0.02 units. Highly concentrated samples were diluted by weight such that the recorded optical density was within the linear response range of the chromophore.

Host Chromosomal DNA

Host chromosomal DNA contamination was assessed using PCR analysis, employing oligonucleotide primers complementary to a ubiquitous element of the *E. coli* genome. Standards of pTX0161 purified by double density gradient ultracentrifugation (Sambrook et al., Molecular Cloning: a laboratory manual, Nolan et al., (Eds), Cold Spring Harbor Laboratory Press, New York, 1989) were spiked in duplicate with varying percentages (w/w) of DH1 host chromosomal DNA. An identical quantity of the pTX0161 was also subjected to the reaction and analysed alongside the other samples by 1% agarose gel electrophoresis. Maximum contamination levels were derived based on a comparison of the intensity of the host chromosomal DNA spiked standards against the sample being tested.

Endotoxin Contamination

Endotoxin contamination was assessed using the KQCL kinetic chromogenic assay (Biowhittaker UK Ltd). Product was diluted to a range known to overcome interference. Positive product controls were included to confirm that no inhibition or enhancement of the reaction cascade by sample or buffer components had occurred.

EXAMPLE 1

Figure 1:
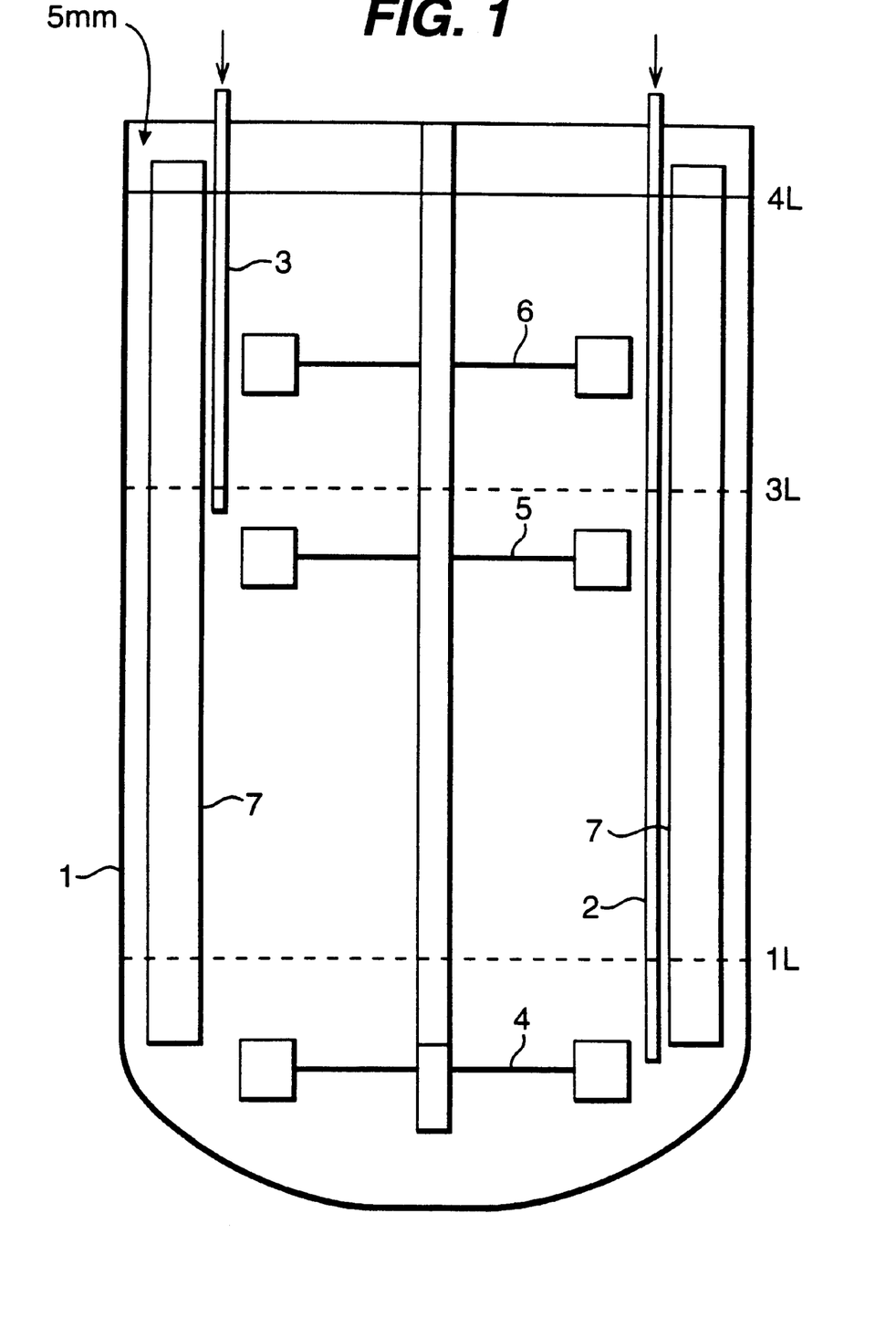
FIG. 1 is a schematic diagram showing a 5 l vessel according to the present invention.

The vessel (1) has a volume of 5 l, an internal diameter of 165 mm and is operated with two feedlines (2, 3) in the vessel (1). The vessel (1) has three InterMig impellers (4, 5, 6) positioned 18 mm, 105 mm and 155 mm from the bottom of the vessel (1). The impellers are 116 mm in length. The first feedline (2) is positioned so that fluid is delivered at the same level as the lowest impeller (4). The first feedline (2) is used to add a cell suspension and subsequently a lysis buffer to the vessel (1). The second feedline (3) is positioned so that fluid is delivered at the same level as the second impeller (5). The second feedline (3) is used to add a neutralisation buffer.

The vessel (1) also has four baffles (7) spaced equally around the inner vertical wall of the vessel (1) which are substantially parallel to the axis of rotation of the impellers (4, 5, 6). Each baffle (7) has a width of 15 mm and is approximately 315 mm in length. The baffles (7) are spaced from the internal wall of the vessel (1) by a 5 mm gap. The clearance between the baffles and the arc formed by rotation of the impellers is 5 mm.

The feedlines (2, 3) are constructed from 5 or 10 ml pipettes with the bottom tapered section removed and the plugs removed from the top section connected to lengths of peristaltic pump tubing. The feedlines (2, 3) have an internal diameter of approximately 4 mm.

The vessel (1) has an aspect ratio of 1.1 (183/165).

Lysis Protocol

A 180 g/l (wet weight) solution of *E. coli* DH1 cells containing plasmid pTX0161 was generated by resuspending 180 g of frozen cells into cell suspension buffer (50 mM Tris base, 10 mM EDTA pH8.0) using a Silverson high shear lab mixer (Silverson Machines Ltd.) as indicated above. The solution was mixed until a homogeneous solution was obtained. The volume was then adjusted to 1 l with cell suspension buffer. The solution was then transferred to the lysis vessel (1) and mixed at 75 rpm. 100 mg of RNaseA was then added to the solution and incubated for 5 minutes with stirring.

2 l of lysis buffer (0.155M NaOH/1% SDS), at a flow rate of 1 l/min were added and the timing of the lysis started at this point. When all the lysis buffer had been added (2 minutes), the stirrer speed was increased to 125 rpm and maintained until all the cells had been solubilised (4 minutes after lysis started). The impellers were then switched off.

At 9 minutes 30 seconds after lysis started the contents of the vessel were stirred at a speed of 75 rpm. At 10 minutes after lysis was started, 1 l of the neutralisation buffer (3M KAc, 10 mM EDTA pH5.5) was added at a flow rate of 500 ml/min. When the top impeller (6) was completely covered, the impeller speed was raised to 100 rpm and maintained until the Weissenburg effect was lost (12 minutes). Lysis was then regarded as complete and the impellers switched off.

The vessel contents were cooled for 40 minutes by circulating chilled water at 5_C around the vessel to reduce the temperature of the contents to about 10_C. The vessel contents were then filtered via a 100 μm bag filter (Plastok Holdings Ltd., Birkenhead, England) and 5 μm depth filter (Millipore Ltd., Watford, England) as described above. The collected filtrate was then purified via expanded bed chromatography as described above.

It should be noted that the generation of homogenous cell suspension prior to lysis can be achieved using the vessel of the present invention.

Yield and contamination measurements were made as described above.

Results of plasmid yield using different plasmid host strain combinations

| Plasmid | Cell Concentration | Yield (μg/g wet weight) | |
|---|---|---|---|
| | | Manual Lysis | Lysis Vessel |
| PTX0161 | 120 g/l | 351 | 349 |
| PTX0340 | 240 g/l 180 g/l | 328280 | 345277 |
| | 180 g/l | 165 | 200 |

Chromosomal DNA Contamination

| Plasmid | Cell Concentration | % cDNA | |
|---|---|---|---|
| | | Manual Lysis | Lysis Vessel + Cobra Process |
| PTX061 | 180 g/l | 5 | <2 |
| | 240 g/l | 2–4 | <2 |
| PTX0340 | 180 g/l | 4–5 | <2 |
| | 180 g/l | 4–5 | <2 |

Endotoxin Contamination

| Plasmid | Endotoxin (Eu/mg) |
|---|---|
| PTX0161 | 7.4 |
| PTX0161 | 21.2 |
| PTX034O | 616 |

EXAMPLE 2

Description of the Lysis Vessel

Figure 2:
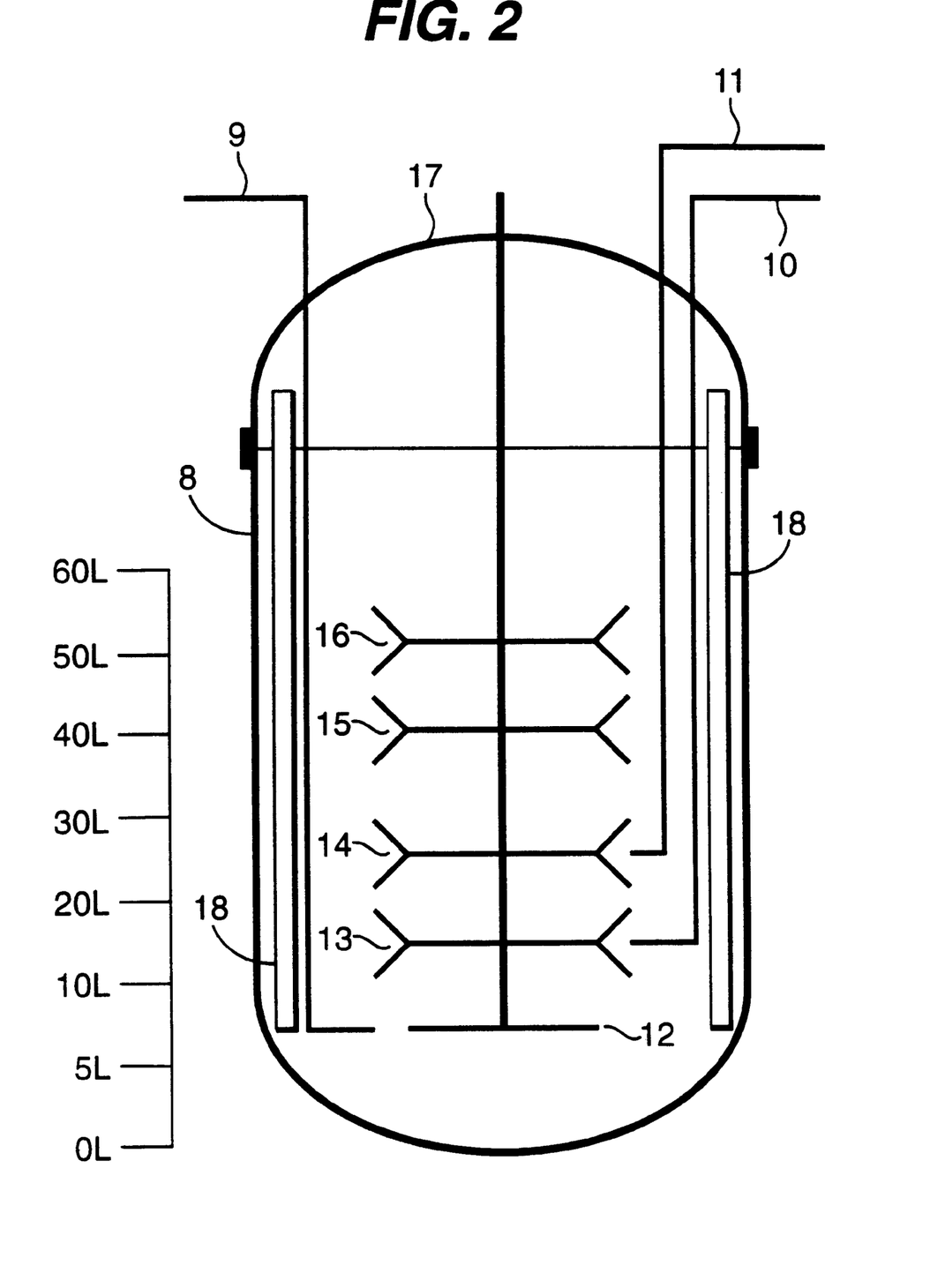
FIG. 2 is a schematic diagram showing a 60 l vessel according to the present invention.

The vessel (8) has a volume of 60 l, an internal diameter of 455 mm and is operated with three feedlines (9, 10, 11). The vessel has a lid (17) which forms a hermetic seal with the main body of the vessel. The vessel has five impellers (12, 13, 14, 15, 16). The first impeller (12) is a propeller type impeller having the same pitch angle as an INTERMIG® impeller (see FIG. 3) with the distal forked heads (16) removed. The first impeller (12) is 190 mm in length. The remaining four impellers are INTERMIG® impellers as shown in FIG. 3 and are 280 mm in length. The impellers are positioned 45 mm, 100 mm, 185 mm, 270 mm and 370 mm from the bottom of the vessel, respectively. The first two impellers (12, 13) are therefore within the bottom 15 l level of the vessel (8) and are used to stir the cell suspension. The third and fourth impellers (14, 15) are placed in the 15 l to 45 l levels of the vessel (8) and with the first two impellers (12, 13) will be used to mix cells with the lysis solution. The fifth impeller (16) is placed in the 45 to 60 l level of the vessel (8) and with the first four impellers (12, 13, 14, 15) will be used to mix the neutralised solution.

The first feedline (9) is movable between the level of the first and second impellers (12, 13). In this example, the feedline is positioned to deliver fluid at the same level as the first impeller (12). The second feedline (10) is movable between the level of the first and second impeller (12, 13). In this example, the feedline is initially positioned to deliver fluid at the same level as the second impeller (13). The third feedline (11) is movable between the level of the second, third, fourth and fifth impellers (13, 14, 15, 16). In this example, the feedline is initially positioned at the level of the third impeller (14). The feedlines (9, 10) are fed by peristaltic pumps (Watson Marlow 600 series fitted 1.75 cm ID silicone tubing (Watson Marlow Ltd., Falmouth, England) under manual control.

The vessel (8) also has four baffles (18) spaced equally around the inner vertical wall of the vessel (8) which are substantially parallel to the axis of rotation of the impellers (12, 13, 14, 15, 16). Each baffle (18) has a width of 45 mm and is approximately 330 mm in length. The baffles (18) are spaced from the internal wall of the vessel (8) by a 10 mm gap.

The vessel (8) has an aspect ratio of 0.97 (440/455).

Lysis Protocol 15 l solution of cell suspension of *E.coli* DH1 cells containing plasmid pTX0161 at a concentration of 120 g/l was generated by resuspending 1200 g of frozen cells into cell suspension buffer (50 mM Tris base, 10 mM EDTA pH.8) at 4° C. Resuspension was achieved using a Silverson high shear mixer (Silverson Machines Ltd) as described above. The solution was mixed until a homogeneous solution was achieved, the volume was then adjusted by weight to 15 l using cell suspension buffer. The cells were generated by the fermentation protocol outlined above and harvested by centrifugation and stored at −80° C. prior to use.

The cell suspension was transferred to the lysis vessel (8) and agitated at a speed of 8 rpm. 1.5 g of RNase (Sigma Chemicals) resuspended in 15 ml of cell suspension buffer was added to the cell suspension and allowed to incubate for 5 minutes at room temperature.

The impeller speed was increased to 44 rpm and 30 l of cell lysis buffer (0.155M NaOH, 1.0% SDS) was added to the solution. Initially this was added through the first and the second feedlines (9, 10) at a flow rate of 7.4 l/min. When third impeller (14) was completely covered with liquid, lysis buffer was also added via the third feedline (11) at a flow rate of 7.4 l/min. Addition of the lysis solution was completed in less than 2 minutes. The solution was then stirred for a further 2 minutes after which the impellers were stopped and the lysate allowed to incubate.

The height of the third feedline (11) previously at the level of the third impeller (14) was raised to the level of the fourth impeller (15).

Ten minutes after the start of the addition of the lysis buffer the impellers were switched on at a speed of 74 rpm and 15 l of neutralisation buffer (3M Potassium Acetate, 10 mM EDTA pH5.5 at 4° C.) was added via all the feedlines (9, 10, 11) simultaneously at a flow rate of 3.75 l/min. This addition was completed in less than 2 minutes after which the impeller speed was reduced to 26 rpm and these conditions were maintained for an additional 3 minutes after which impeller speed was reduced to 16 rpm for a further 6 minutes.

The vessel contents were then filtered via a 100 μm bag filter (Plastok Holdings Ltd., Birkenhead, England) and 5

μm depth filter (Millipore Ltd., Watford, England) as described above. The collected filtrate was then purified via expanded bed chromatography as described above.

Yield and contamination measurements were made as described above.

Results

| Plasmid Yield | 344 μg/g wet weight |
|---|---|
| Endotoxin content | 13 Eu/mg |
| Chromosomal DNA | 4% |

EXAMPLE 3

The lysis vessel was as described in Example 1 with the following modifications. Mixing was either by three INTERMIG impellers, positioned at 50 mm intervals from the base of the vessel, or by two split helical ribbons, with the bottom impeller 3.8 cm from the base of the vessel and the two impellers 5.8 cm apart.

Lysis Protocol

A 120 g/L of cell suspension of DH1 host strain was prepared using a high shear mixer and then transferred to the lysis vessel and mixed at 125 rpm. 2L lysis buffer was added at a flow rate of 1L/min to this solution and a mixing speed of 125 rpm was maintained throughout the lysis, incubation and neutralisation steps. On completion of the incubation, 1L of neutralisation buffer was added at a flow rate of 1L/min.

Determination of Motor Torque

Motor torque was determined using a Visco-Mix rheometer supplied by Coesfield, Mess Technich GMBH. Germany. This was connected to the stirrer shaft to which various types of impellers were attached and the lysis performed as described.

Results

Figure 5:
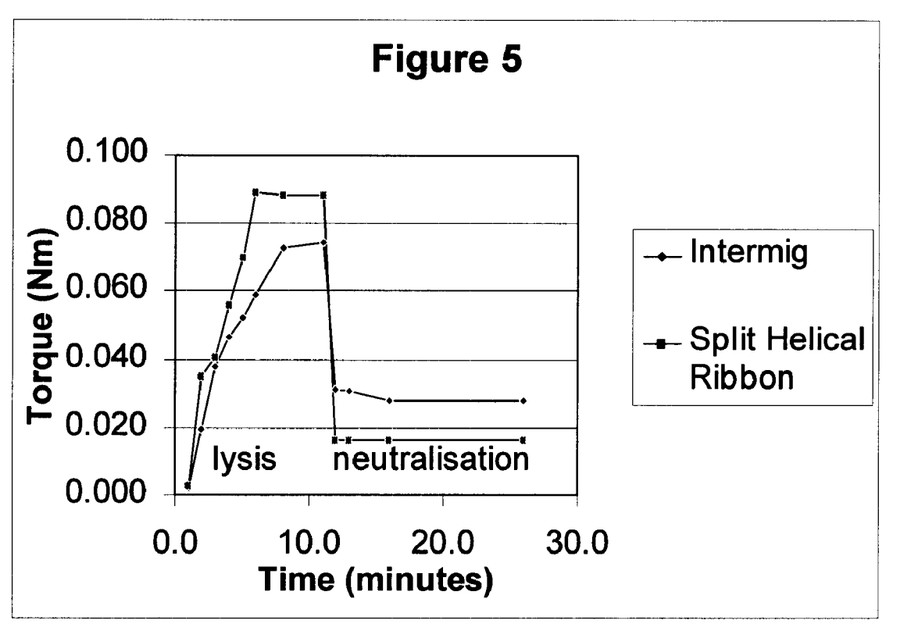
FIG. 5 shows a graph of torque measurements during mixing of a cell lysis reaction, using either INTERMIG or split helical ribbon type impellers.

The results shown in FIG. 5 show a rapid increase in motor torque during the addition of the lysis buffer. This is indicative of changes in the rheological properties of the lysis solution. The graph shows that for both types of impeller that a stable state is achieved less than 3 mins after the completion of the addition of the lysis buffer, indicating that no further changes in rheological properties are occurring and from which complete lysis is inferred.

Upon the addition of the neutralisation buffer, a dramatic decrease in motor torque is seen; followed by a stable state, again indicating that no further changes in rheological properties are occurring and that complete neutralisation has occurred.

All the references referred to herein are hereby incorporated by reference in their entireties.

It will of course be understood that the present invention has been described purely by way of example, and that modifications of detail can be made within the scope of the invention as defined in the following claims.

What is claimed is:

1. A vessel for mixing a cell suspension and/or a cell lysate containing chromosomal DNA and a desired product, wherein the vessel comprises:
   (a) one or more low power number impellers positioned so that the impeller or impellers give even dissipation of energy throughout the contents of the vessel;
   (b) one or more feedlines enabling the addition of fluids to a well-mixed zone formed around the distal end of one or more of the impellers; and
   (c) one or more baffles spaced substantially equally around the inner surface of the vessel, wherein the one or more baffles extend substantially parallel to the axis of rotation of the impellers.

2. The vessel according to claim 1 having 4 baffles.

3. The vessel according to claim 1, wherein the baffles have a width which is 6 to 15% of the internal diameter of the vessel.

4. The vessel according to claim 1, wherein the one or more impellers are interference multistage counter flow impellers.

5. The vessel according to claim 1, wherein the one or more impellers are helical ribbon impellers.

6. The vessel according to claim 5, wherein the one or more helical ribbon impellers are sectioned helical ribbon impellers.

7. The vessel according to claim 1, wherein the feedlines are a tube or a series of tubes present on the inner surface of the vessel which deliver fluid at substantially the same level in the vessel as an impeller.

8. The vessel according to claim 7, wherein one or more of the feedlines are movable within the vessel so that the level at which fluids are added can be altered during mixing.

9. The vessel according to claims 1, wherein the feedline is a conduit within the axle carrying the impellers which passes through one or more of the impellers and delivers fluid adjacent to the distal end of the one or more impellers.

10. The vessel according to claim 1, wherein the aspect ratio is 0.1 to 2.5.

11. The vessel according to claim 1, wherein the ratio of the impeller length to the internal diameter of the vessel is greater than 0.5.

12. A method for using a vessel according to any one of the preceding claims in the lysis of cells of a cell suspension, which cells contain chromosomal DNA and a desired product, said method comprising the one or more impellers rotating at a speed selected such that efficient mixing is obtained without generating mechanical stresses sufficient to lead to substantial fragmentation of chromosomal DNA or flocs of aggregated material.

13. A method for monitoring the degree of lysis of a cell suspension in a vessel whose contents are mixed by rotating one or more impellers, comprising measuring the torque applied to the axle of the impeller, wherein the torque increases in proportion to the degree of cell lysis until lysis is complete, when it stabilises at a maximum value.

14. The method according to claim 13, wherein cell lysis causes an increase of torque of between 500% and 1500% over the initial torque applied to the axle of the impeller to mix the unlysed cell suspension.

15. The method according of claim 13, additionally comprising the step of neutralising the contents of said vessel after cell lysis is complete.

16. The method according to claim 15, wherein the degree of neutralisation of the cell lysate the monitored by measuring the torque applied to the axle of the impeller.

17. The method according to claim 16, wherein complete neutralisation of the cell lysate is indicated by a decrease in torque to less than 50% of the maximum torque applied to the axle during the lysis stage of the reaction.

18. A method for preparing a desired product from a cell suspension in a vessel, comprising the steps of lysing said cells by alkaline lysis to give a cell lysate, neutralising said cell lysate and preparing the desired product from the cell lysate, wherein the contents of said vessel are mixed by rotating one or more impellers, and wherein progress of the lysis and neutralisation reactions is monitored using a method according to any one of claims 14–17.

19. The method according to claim 18, wherein the desired product is plasmid DNA.

20. The method according to claim 18, wherein the desired product is a protein.

* * * * *

UNITED STATES PATENT AND TRADEMARK OFFICE
CERTIFICATE OF CORRECTION

PATENT NO.    : 6,395,516 B1
DATED         : May 28, 2002
INVENTOR(S)   : Alvin William Nienow et al.

It is certified that error appears in the above-identified patent and that said Letters Patent is hereby corrected as shown below:

Title page,
Item [75], Inventors, please delete "Hitchock" and insert -- Hitchcock -- therefor; and please delete "Sussex" and insert -- Surrey -- therefor.

Column 1,
Line 38, "DNA☐s" should read -- DNA's --.

Column 18,
Line 20, "claims" should read -- claim --.

Signed and Sealed this

Twelfth Day of April, 2005

JON W. DUDAS
*Director of the United States Patent and Trademark Office*